United States Patent
Ito et al.

(10) Patent No.: US 10,286,285 B2
(45) Date of Patent: May 14, 2019

(54) DISPLAY METHOD, DISPLAY APPARATUS, MOTION ANALYSIS SYSTEM, MOTION ANALYSIS PROGRAM, AND RECORDING MEDIUM

(71) Applicant: SEIKO EPSON CORPORATION, Tokyo (JP)

(72) Inventors: Tsuyoshi Ito, Suwa (JP); Kazuhiro Shibuya, Shiojiri (JP); Kenya Kodaira, Azumino (JP)

(73) Assignee: SEIKO EPSON CORPORATION, Tokyo (JP)

( * ) Notice: Subject to any disclaimer, the term of this patent is extended or adjusted under 35 U.S.C. 154(b) by 24 days.

(21) Appl. No.: 15/401,207

(22) Filed: Jan. 9, 2017

(65) Prior Publication Data

US 2017/0203181 A1  Jul. 20, 2017

(30) Foreign Application Priority Data

Jan. 15, 2016 (JP) ................. 2016-005849

(51) Int. Cl.
| | |
|---|---|
| *A63B 69/36* | (2006.01) |
| *A63B 24/00* | (2006.01) |
| *A63B 71/06* | (2006.01) |
| *A61B 5/11* | (2006.01) |
| *G06K 9/00* | (2006.01) |

(Continued)

(52) U.S. Cl.
CPC ............ *A63B 69/3632* (2013.01); *A61B 5/11* (2013.01); *A61B 5/1122* (2013.01); *A61B 5/6895* (2013.01); *A61B 5/7445* (2013.01); *A63B 24/0003* (2013.01); *A63B 71/0619* (2013.01); *G06K 9/00342* (2013.01); *A61B 2503/10* (2013.01); *A63B 2071/0647* (2013.01); *A63B 2071/0663* (2013.01); *A63B 2102/02* (2015.10); *A63B 2102/04* (2015.10); *A63B 2102/16* (2015.10); *A63B 2102/18* (2015.10); *A63B 2102/182* (2015.10); *A63B 2220/34* (2013.01); *A63B 2220/44* (2013.01); *A63B 2220/807* (2013.01); *A63B 2225/50* (2013.01)

(58) Field of Classification Search
CPC .................................. A63B 69/3632
See application file for complete search history.

(56) References Cited

U.S. PATENT DOCUMENTS 9,211,439 B1 * 12/2015 Pedenko ............ A63B 24/0006
2009/0005188 A1   1/2009 Iwatsubo et al.
(Continued)

FOREIGN PATENT DOCUMENTS

| JP | 2009-005760 A | 1/2009 |
| JP | 2014-100341 A | 6/2014 |

*Primary Examiner* — Omkar A Deodhar
(74) *Attorney, Agent, or Firm* — Oliff PLC

(57) ABSTRACT

A display method includes acquiring first attitude information of the hands of a subject holding an exercise equipment during standing still on the basis of an output from an inertial sensor (sensor unit) which measures a swing action of the subject (user) performing a swing with the exercise equipment (golf club) and is attached to at least one of the exercise equipment and the subject, acquiring second attitude information of the hands of the subject holding the exercise equipment at impact on the basis of an output from the inertial sensor, and displaying at least one of the first attitude information and the second attitude information.

28 Claims, 7 Drawing Sheets

(51) Int. Cl.
*A61B 5/00* (2006.01)
*A63B 102/02* (2015.01)
*A63B 102/04* (2015.01)
*A63B 102/16* (2015.01)
*A63B 102/18* (2015.01)

(56) References Cited

U.S. PATENT DOCUMENTS

| | | | |
|---|---|---|---|
| 2011/0230274 A1* | 9/2011 | Lafortune | A43B 3/0005 473/217 |
| 2012/0157241 A1* | 6/2012 | Nomura | A63B 69/0002 473/422 |
| 2014/0228141 A1* | 8/2014 | Sakyo | A63B 24/0006 473/223 |
| 2016/0045786 A1* | 2/2016 | Cottam | H04M 1/04 473/409 |

* cited by examiner

DISPLAY METHOD, DISPLAY APPARATUS, MOTION ANALYSIS SYSTEM, MOTION ANALYSIS PROGRAM, AND RECORDING MEDIUM

CROSS-REFERENCE TO RELATED APPLICATIONS

The present application claims priority to Japanese Patent Application JP 2016-005849, filed Jan. 15, 2016, the entire disclosure of which is hereby incorporated by reference herein.

BACKGROUND

1. Technical Field

Various embodiments of the present invention relate to a display method, a display apparatus, a motion analysis system, a motion analysis program, and a recording medium.

2. Related Art

In the related art, there is a technique in which a swing is imaged by using a plurality of cameras in order to check a swing of an exercise equipment, for example, a golf swing, and a captured image is processed by using a three-dimensional coordinate measurement system (for example, a direct linear transformation (DLT) method) (refer to JP-A-2009-5760). There is a technique in which an impact timing, that is, a ball hitting timing during a swing is detected by using a motion sensor, and then the swing is analyzed (refer to JP-A-2014-100341).

However, in the techniques disclosed in JP-A-2009-5760 and JP-A-2014-100341, it is difficult to objectively determine an attitude of the hands holding a golf club during a swing, for example, a swing related attitude such as "hands-up" or "hands-down".

SUMMARY

An advantage of some aspects of the invention is to solve at least a part of the problems described above, and various embodiments of the invention can be implemented as the following aspects or application examples.

Application Example 1

A display method according to this application example includes acquiring first attitude information of the hands of a subject holding an exercise equipment during standing still on the basis of an output from an inertial sensor which measures swing actions of the subject performing a swing with the exercise equipment and is attached to at least one of the exercise equipment and the subject; acquiring second attitude information of the hands of the subject holding the exercise equipment at impact on the basis of an output from the inertial sensor; and displaying at least one of the first attitude information and the second attitude information.

According to the display method of this application example, since at least one of the first attitude information of the hands of the subject during standing still and the second attitude information of the hands of the subject at impact, acquired on the basis of outputs from the inertial sensor is displayed, it is possible to easily visually recognize an attitude related to the hands of the subject in a swing, such as "hands-up" or "hands-down". Consequently, it is possible to objectively recognize or determine an attitude of the hands of the subject holding a golf club during a swing.

Application Example 2

It is preferable that the display method of the application example further includes acquiring attitude difference information between the first attitude information and the second attitude information, and, in the displaying, the attitude difference information is displayed.

According to this application example, since the attitude difference information between the first attitude information and the second attitude information is displayed, it is possible to visually recognize a difference between an attitude during standing still and an attitude at impact, and thus to objectively determine an attitude difference caused by a swing action or a change in an attitude difference for each swing action. Consequently, it is possible to easily cope with an attitude difference between an attitude during standing still and an attitude at impact.

Application Example 3

It is preferable that the display method of the application example further includes acquiring a swing trajectory of the subject on the basis of an output from the inertial sensor, and, in the displaying, the swing trajectory is displayed.

According to this application example, the swing trajectory of the subject based on an output from the inertial sensor is displayed, and thus it is possible to easily visually recognize a series of swing actions. Consequently, it is possible to more easily determine a swing state of the subject.

Application Example 4

It is preferable that the display method of the application example further includes capturing an image of a swing of the subject, and, in the displaying, the captured image of the swing is displayed.

According to this application example, a captured image of a swing of the subject is displayed, and thus it is possible to visually recognize a series of swing actions as an image. Consequently, it is possible to determine a swing action while visually recognizing an actual swing action of the subject.

Application Example 5

In the display method of the application example, it is preferable that in the displaying, at least one of a first straight line based on the first attitude information and the second straight line based on the second attitude information is displayed.

According to this application example, it is possible to represent an attitude of the hands of the subject or the exercise equipment according to either one of the first straight line and the second straight line which are displayed, and thus to easily visually recognize an attitude of the hands of the subject or the exercise equipment.

Application Example 6

In the display method of the application example, it is preferable that, in the displaying, information is displayed in a front view viewed from a direction intersecting a hitting surface of the exercise equipment.

According to this application example, a state of an inclination (an inclination of an exercise equipment) connecting the hands of the subject to a target position during standing still or at impact can be displayed so as to be easily viewed and easily understood, and thus it is possible to easily point out a state (quality) of the inclination or a variation in the inclination.

Application Example 7

In the display method of the application example, it is preferable that the front view is a front view viewed from a target side or a front view viewed from an opposite side to the target side.

According to this application example, a state of an inclination (an inclination of an exercise equipment) connecting the hands of the subject to a target position during standing still or at impact can be displayed so as to be easily viewed and easily understood.

Application Example 8

A display apparatus according to this application example includes a first generation section that generates first attitude information of the hands of a subject holding the exercise equipment during standing still on the basis of an output from an inertial sensor which measures swing actions of the subject performing a swing with the exercise equipment and is attached to at least one of the exercise equipment and the subject; a second generation section that generates second attitude information of the hands of the subject holding the exercise equipment at impact on the basis of an output from the inertial sensor; and a display section that displays at least one of the first attitude information and the second attitude information.

According to the display apparatus of this application example, at least one of the first attitude information of the hands of the subject during standing still, generated by the first generation section, and the second attitude information of the hands of the subject at impact, generated by the second generation section, on the basis of outputs from the inertial sensor, is displayed on the display section. Therefore, it is possible to easily recognize a state of an attitude related to the hands of the subject in a swing, such as "hands-up" or "hands-down" by viewing the display section. Consequently, it is possible to easily and objectively determine the quality of an attitude of the hands of the subject holding a golf club during a swing by using the display apparatus of the application example.

Application Example 9

It is preferable that the display apparatus of the application example further includes a third generation section that generates attitude difference information between the first attitude information and the second attitude information, and the display section displays the attitude difference information.

According to this application example, the attitude difference information between the first attitude information and the second attitude information is displayed on the display section, and thus it is possible to easily visually recognize a difference between an attitude during standing still and an attitude at impact. Therefore, it is possible to objectively determine an attitude difference caused by a swing action or a change in an attitude difference for each swing action, and thus to easily cope with an attitude difference between an attitude during standing still and an attitude at impact.

Application Example 10

In the display apparatus of the application example, it is preferable that the display section displays a swing trajectory of the subject.

According to this application example, the swing trajectory of the subject based on an output from the inertial sensor is displayed on the display section, and thus it is possible to easily visually recognize a series of swing actions. Consequently, it is possible to more easily determine a swing state of the subject.

Application Example 11

It is preferable that the display apparatus of the application example further includes an imaging section that captures an image of the swing of the subject, and the display section displays the captured image of the swing.

According to this application example, a captured image of a swing of the subject is displayed on the display section, and thus it is possible to visually recognize a series of swing actions as an image. Consequently, it is possible to determine a swing action of the subject while visually recognizing an actual swing action as an image.

Application Example 12

In the display apparatus of the application example, it is preferable that the display section displays at least one of a first straight line based on the first attitude information and the second straight line based on the second attitude information.

According to this application example, it is possible to represent an attitude of the hands of the subject or the exercise equipment according to either one of the first straight line and the second straight line which are displayed on the display section, and thus to easily visually recognize an attitude of the hands of the subject or the exercise equipment.

Application Example 13

In the display apparatus of the application example, it is preferable that the display section displays information in a front view viewed from a direction intersecting a hitting surface of the exercise equipment.

According to this application example, a state of an inclination (an inclination of an exercise equipment) connecting the hands of the subject to a target position during standing still or at impact can be displayed on the display section so as to be easily viewed and easily understood. Thus, it is possible to easily perceive or point out a state (quality) of the inclination (an inclination of an exercise equipment) or a variation in the inclination.

Application Example 14

In the display apparatus of the application example, it is preferable that the front view is a front view viewed from a target side or a front view viewed from an opposite side to the target side.

According to this application example, a state of an inclination (an inclination of an exercise equipment) connecting the hands of the subject to a target position during standing still or at impact can be displayed on the display section so as to be easily viewed and easily understood.

Application Example 15

A motion analysis system according to this application example includes the display apparatus described in anyone of the application examples; and the inertial sensor.

According to the motion analysis system of this application example, at least one of the first attitude information of the hands of the subject during standing still, generated by the first generation section, and the second attitude information of the hands of the subject at impact, generated by the second generation section, on the basis of outputs from the inertial sensor which is attached to at least one of the exercise equipment and the subject, is displayed on the display apparatus. Therefore, it is possible to easily recognize a state of an attitude related to the hands of the subject in a swing, such as "hands-up" or "hands-down" by viewing the display section of the display apparatus. Consequently, it is possible to easily and objectively recognize an attitude of the hands of the subject holding a golf club during a swing or to determine the quality of the attitude by using the motion analysis system of the application example.

Application Example 16

A motion analysis program according to this application example causes a computer to execute acquiring first attitude information of the hands of a subject holding the exercise equipment during standing still on the basis of an output from an inertial sensor which measures swing actions of the subject performing a swing with the exercise equipment and is attached to at least one of the exercise equipment and the subject; acquiring second attitude information of the hands of the subject holding the exercise equipment at impact on the basis of an output from the inertial sensor; and displaying at least one of the first attitude information and the second attitude information.

According to the motion analysis program of this application example, a computer is caused to display at least one of the first attitude information of the hands of the subject during standing still, generated by a first generation section, and the second attitude information of the hands of the subject at impact, generated by a second generation section, on the basis of outputs from the inertial sensor which is attached to at least one of the exercise equipment and the subject. Therefore, it is possible to easily recognize a state of an attitude related to the hands of the subject in a swing, such as "hands-up" or "hands-down" by viewing the state. Consequently, it is possible to easily and objectively recognize an attitude of the hands of the subject holding a golf club during a swing or to determine the quality of the attitude by using the motion analysis program of the application example.

Application Example 17

A recording medium according to this application example stores a program causing a computer to execute acquiring first attitude information of the hands of a subject holding the exercise equipment during standing still on the basis of an output from an inertial sensor which measures swing actions of the subject performing a swing with the exercise equipment and is attached to at least one of the exercise equipment and the subject; acquiring second attitude information of the hands of the subject holding the exercise equipment at impact on the basis of an output from the inertial sensor; and displaying at least one of the first attitude information and the second attitude information.

According to the recording medium of this application example, a computer can be executed on the basis of the stored program. Consequently, at least one of the first attitude information of the hands of the subject during standing still, generated by a first generation section, and the second attitude information of the hands of the subject at impact, generated by a second generation section, on the basis of outputs from the inertial sensor which is attached to at least one of the exercise equipment and the subject, is displayed on the display apparatus. Through the display, it is possible to easily recognize a state of an attitude related to the hands of the subject in a swing, such as "hands-up" or "hands-down".

BRIEF DESCRIPTION OF THE DRAWINGS

The various embodiments of the invention will be described with reference to the accompanying drawings, wherein like numbers reference like elements.

DESCRIPTION OF EXEMPLARY EMBODIMENTS

Hereinafter, various embodiments of the invention will be described with reference to the drawings. The embodiments described below are not intended to improperly limit the content of one or more embodiments of the invention disclosed in the appended claims. In addition, all constituent elements described below are not essential constituent elements of one or more embodiments of the invention.

Figure 1:
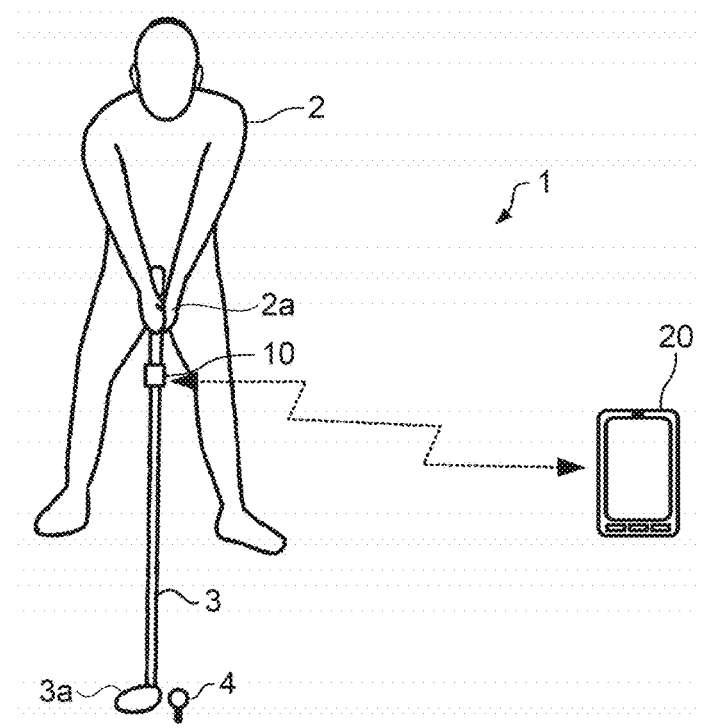
FIG. 1 is a diagram illustrating a summary of a motion analysis system (swing analysis system).
Figure 2:
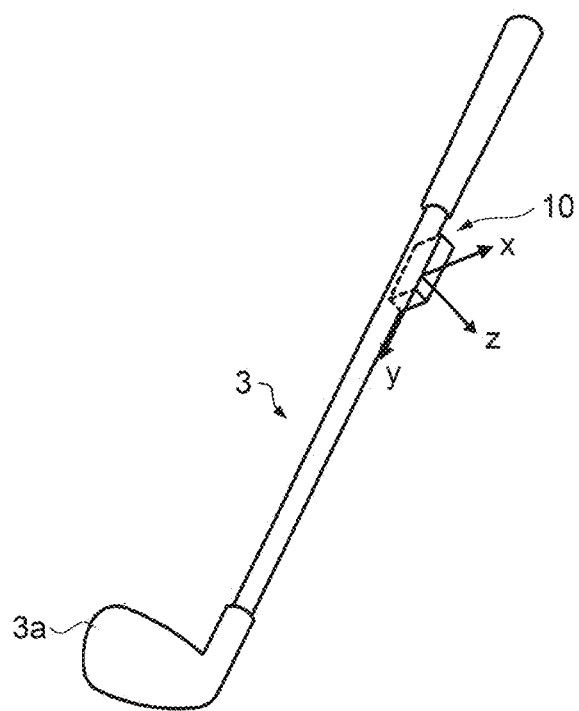
FIG. 2 is a diagram illustrating examples of a position at which and a direction in which the sensor unit is attached.
Figure 3:
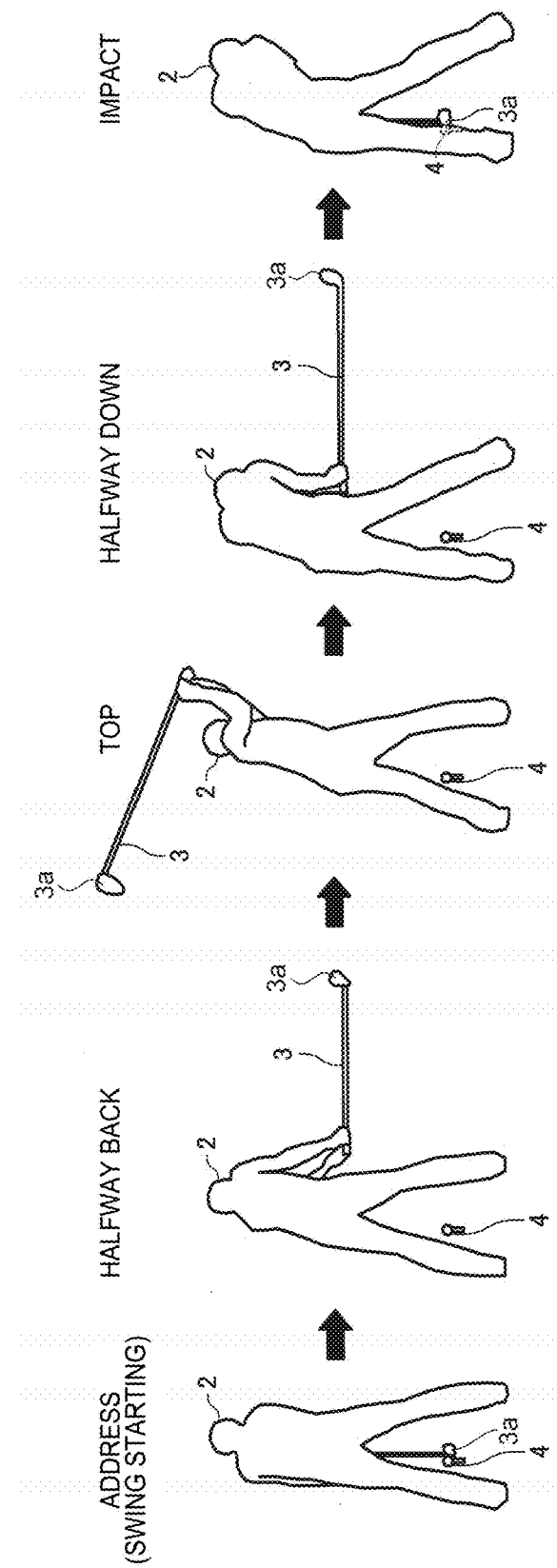
FIG. 3 is a diagram illustrating swing actions.
Figure 4:
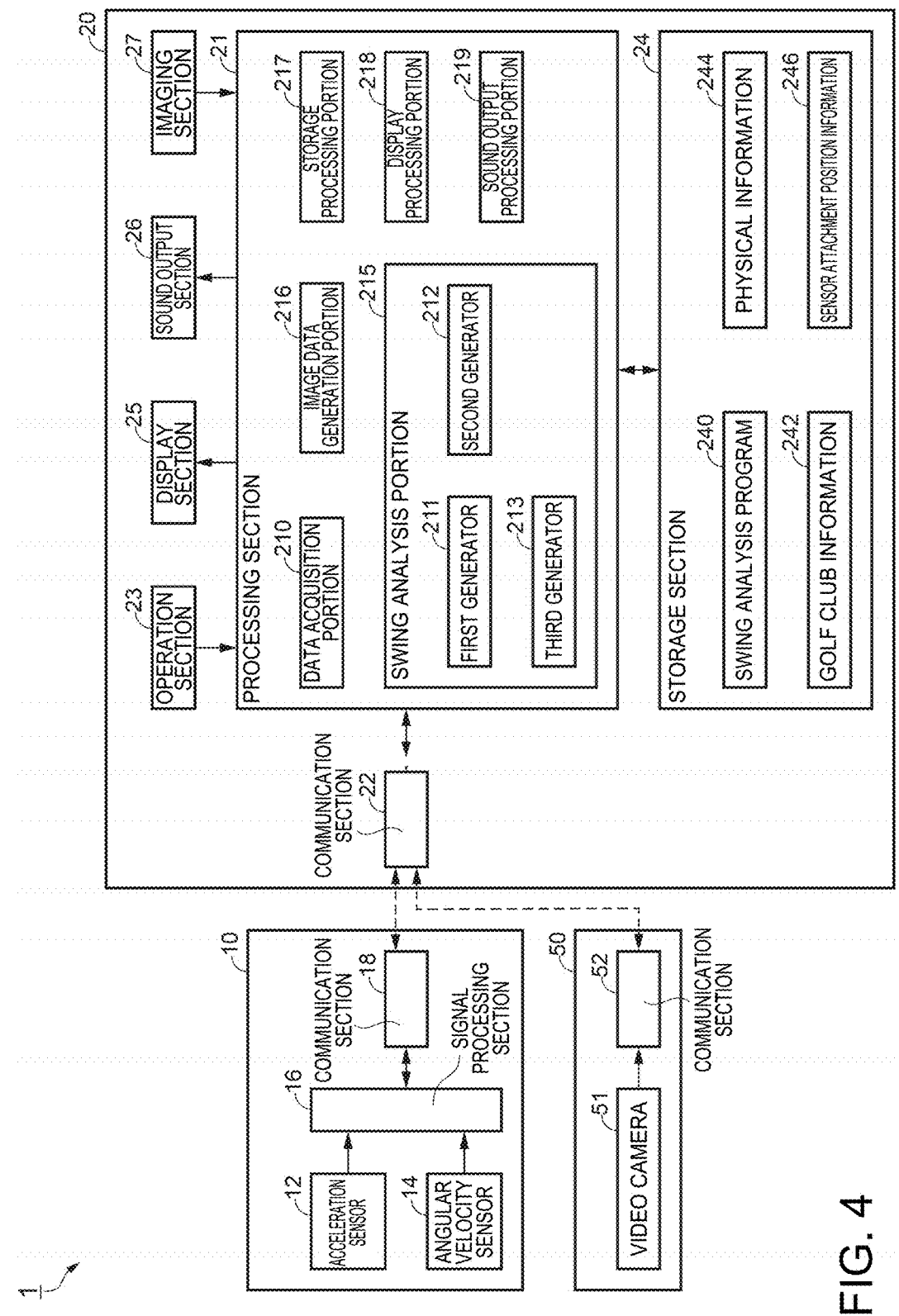
FIG. 4 is a diagram illustrating a configuration example of the motion analysis system (swing analysis system).

Swing Analysis (Motion Analysis) System 1-1. Configuration of Swing Analysis (Motion Analysis) System FIG. 1 is a diagram illustrating a summary of a swing analysis system (an example of a motion analysis system) of the present embodiment. FIG. 2 is a diagram illustrating examples of a position at which and a direction in which the sensor unit is attached. FIG. 3 is a diagram illustrating a series of swing actions. FIG. 4 is a diagram illustrating a configuration example of the motion analysis system (swing analysis system).

As illustrated in FIG. 1, a swing analysis system 1 of the present embodiment is configured to include a sensor unit 10 (an example of an inertial sensor), and a motion analysis display apparatus 20 as a display apparatus. The swing analysis system 1 may be configured to include a recorder 50 as illustrated in FIG. 4. The swing analysis system 1 analyzes a swing (hereinafter, referred to as a golf swing) of a golf club 3 performed by a user (subject) 2 in order to hit a golf ball 4 as a target. In the present embodiment, a swing analysis apparatus analyzing a golf swing will be exemplified, but a swing analysis apparatus according to one or more embodiments of the invention is applicable to swing analysis of various exercise equipment used to perform swings, such as rackets in tennis, badminton, and table tennis, and bats in baseball or softball.

The sensor unit 10 can measure acceleration generated in each axial direction of three axes and angular velocity generated around each of the three axes by using provided inertial sensors (an acceleration sensor 12 and an angular velocity sensor 14 illustrated in FIG. 4), and is attached to a golf club 3 (an example of an exercise equipment) in the present embodiment.

In the present embodiment, as illustrated in FIG. 2, the sensor unit 10 is attached to a part of a shaft of the golf club 3 so that one axis of three detection axes (an x axis, a y axis, and a z axis), for example, the y axis matches a longitudinal direction of the shaft. Preferably, the sensor unit 10 is attached to a position close to a grip to which impact during ball hitting is hardly forwarded and a centrifugal force is not applied during a swing. The shaft is a shaft portion other than a head 3a of the golf club 3 and also includes the grip. However, the sensor unit 10 may be attached to a part (for example, the hand or a glove) of the user 2 as a subject, and may be attached to an accessory such as a wristwatch.

In the present embodiment, swing analysis (motion analysis) is described by exemplifying a swing of the golf club 3. In a golf swing, for example, a series of swing actions as illustrated in FIG. 3 is performed. Specifically, as illustrated in FIG. 3, the swing actions include actions starting from an address position in a standing still state, and reaching impact at which the golf ball 4 is hit through respective states of halfway back at which the shaft of the golf club 3 becomes horizontal during a backswing after starting a swing (backswing), a top at which the swing changes from the backswing to a downswing, and halfway down at which the shaft of the golf club 3 becomes horizontal during the downswing. After the impact, the series of swing actions is completed through follow-through (not illustrated).

1-2. Configuration of Swing Analysis (Motion Analysis) System

FIG. 4 is a diagram illustrating a configuration example (configuration examples of the sensor unit 10, the motion analysis display apparatus 20, and the recorder 50) of the swing analysis (motion analysis) system 1 of the present embodiment. As illustrated in FIG. 4, in the present embodiment, the sensor unit 10 is configured to include an acceleration sensor 12 and an angular velocity sensor 14 as inertial sensors, a signal processing section 16, and a communication section 18.

The acceleration sensor 12 as an inertial sensor measures respective accelerations in three axial directions which intersect (ideally, orthogonal to) each other, and outputs digital signals (acceleration data) corresponding to magnitudes and directions of the measured three-axis accelerations.

The angular velocity sensor 14 as an inertial sensor measures respective angular velocities in three axial directions which intersect (ideally, orthogonal to) each other, and outputs digital signals (angular velocity data) corresponding to magnitudes and directions of the measured three-axis angular velocities.

The signal processing section 16 receives the acceleration data and the angular velocity data (measured data) from the acceleration sensor 12 and the angular velocity sensor 14, respectively, adds time information thereto, stores the data in a storage portion (not illustrated), adds time information to the stored measured data (an example of attitude or position information) so as to generate packet data conforming to a communication format, and outputs the packet data to the communication section 18.

Ideally, the acceleration sensor 12 and the angular velocity sensor 14 are provided in the sensor unit 10 so that the three axes thereof match three axes (an x axis, a y axis, and a z axis) of an orthogonal coordinate system (sensor coordinate system) defined for the sensor unit 10, but, actually, errors occur in installation angles. Therefore, the signal processing section 16 performs a process of converting the acceleration data and the angular velocity data into data in the xyz coordinate system by using a correction parameter which is calculated in advance according to the installation angle errors.

The signal processing section 16 may perform a process of correcting the temperatures of the acceleration sensor 12 and the angular velocity sensor 14. Alternatively, the acceleration sensor 12 and the angular velocity sensor 14 may have a temperature correction function.

The acceleration sensor 12 and the angular velocity sensor 14 may output analog signals, and, in this case, the signal processing section 16 may A/D convert an output signal from the acceleration sensor 12 and an output signal from the angular velocity sensor 14 so as to generate measured data (acceleration data and angular velocity data), and may generate communication packet data by using the data.

The communication section 18 performs a process of transmitting packet data received from the signal processing section 16 to the motion analysis display apparatus 20, or a process of receiving a control command from the motion analysis display apparatus 20 and sending the control command to the signal processing section 16. The signal processing section performs various processes corresponding to control commands.

The motion analysis display apparatus (display apparatus) 20 is implemented by, for example, an information terminal (client terminal) such as a smart phone, a personal computer, a head mounted display (HMD) 500 which will be described later, or an arm mounted analysis display apparatus 600 which will be described later. The motion analysis display apparatus (display apparatus) 20 is configured to include a processing section 21 (an example of a processing section), a communication section 22, an operation section 23, a storage section 24, a display section 25, a sound output section 26, and an imaging section 27.

The communication section 22 performs a process of receiving packet data transmitted from the sensor unit 10 and sending the packet data to the processing section 21, or a process of transmitting a control command from the processing section 21 to the sensor unit 10.

The operation section 23 performs a process of acquiring operation data from the user (subject) 2 and sending the operation data to the processing section 21. The operation section 23 may be, for example, a touch panel type display, a button, a key, or a microphone. Data acquired from the operation section 23 may include, for example, a swing time (date and time), user identification information (user ID), the sex of the user 2, golf club information 242, physical information 244 of the user 2, and sensor attachment position information 246 corresponding to position information of the sensor unit 10.

The storage section 24 is constituted of, for example, various IC memories such as a read only memory (ROM), a flash ROM, and a random access memory (RAM), or a recording medium such as a hard disk or a memory card.

The storage section 24 stores a program for the processing section 21 performing various calculation processes or a control process, or various programs or data for realizing application functions. Particularly, in the present embodiment, the storage section 24 stores a swing analysis program (motion analysis program) 240 which is read by the processing section 21 and executes a swing analysis process. The swing analysis program 240 may be stored in a non-volatile recording medium (an example of a recording medium) in advance, or the swing analysis program 240 may be received from a server by the processing section 21 via a network, and may be stored in the storage section 24.

The storage section 24 stores the golf club information 242, the physical information 244, and the sensor attachment position information 246 which is position information of the sensor unit 10, as information used for a swing analysis process.

The golf club information 242 is information indicating a specification of the golf club 3 used by the user 2. For example, the user 2 may operate the operation section 23 so as to input golf club information regarding the golf club 3 in use, and the input golf club information may be used as the golf club information 242. Alternatively, in step S100 in FIG. 5 which will be described later, the user 2 may input type numbers of the golf club 3 (alternatively, selects a type number from a type number list) so that specification information (for example, information regarding a length of the shaft, a position of the centroid thereof, a lie angle, a face angle, a loft angle, and the like) for each type number is stored in the storage section 24 in advance. In this case, specification information of an input type number may be used as the golf club information 242.

The physical information 244 is information indicating a physique (a height of the waist, a height of the neck, a length of the arm, and the like) of the user 2. For example, the user 2 may input physical information by operating the operation section 23, and the input physical information may be used as the physical information 244.

The sensor attachment position information 246 is information indicating an attachment position of the sensor unit 10 in the golf club 3. For example, in step S100 in FIG. 5, the user 2 may input an attachment position of the sensor unit 10 and a distance to the grip of the golf club 3 by operating the operation section 23, and the input distance information may be used as the sensor attachment position information 246. Alternatively, the sensor unit 10 may be attached at a defined predetermined position (for example, a distance of 20 cm from the grip), and thus information regarding the predetermined position may be stored as the sensor attachment position information 246 in advance.

The storage section 24 is used as a work area of the processing section 21, and temporarily stores data which is input from the operation section 23, results of calculation executed by the processing section 21 according to various programs, and the like. The storage section 24 may store data which is required to be preserved for a long period of time among data items generated through processing of the processing section 21.

The display section 25 displays a processing result in the processing section 21 as text, a graph, a table, animation, and other images. The display section 25 may be, for example, a CRT, an LCD, a touch panel type display, and a head mounted display (HMD). A single touch panel type display may realize functions of the operation section 23 and the display section 25.

The sound output section 26 outputs a processing result in the processing section 21 as a sound such as a voice or a buzzer sound. The sound output section 26 may be, for example, a speaker or a buzzer.

The imaging section 27 includes a light reception unit (not illustrated) provided with an optical lens (imaging optical system) or a charge coupled device (CCD) (not illustrated). The imaging section 27 may capture an image of a subject (user 2) and store imaging data in the storage section 24, or may send imaging data to an image data generation portion 216, and display image data generated by the image data generation portion 216 on the display section 25.

The processing section 21 performs a process of transmitting a control command to the sensor unit 10, various computation processes on data which is received from the sensor unit 10 via the communication section 22, and other various control processes, according to various programs. By executing the swing analysis program (motion analysis program) 240, the processing section 21 functions as a data acquisition portion 210, a swing analysis portion 215, the image data generation portion 216, a storage processing portion 217, a display processing portion 218, and a sound output processing portion 219.

The data acquisition portion 210 performs a process of receiving packet data which is received from the sensor unit 10 by the communication section 22, acquiring time information and measured data from the received packet data, and sending the time information and the measured data to the storage processing portion 217.

The swing analysis portion 215 includes a first generator 211 which generates first attitude information of the hands 2a (refer to FIG. 1) of the user 2 holding the golf club 3 (exercise equipment) during standing still; a second generator 212 which generates second attitude information of the hands 2a of the user 2 holding the golf club 3 at impact; and a third generator 213 which generates attitude difference information between the first attitude information and the second attitude information. The swing analysis portion 215 performs a process of analyzing a swing of the user 2 by using the measured data output from the sensor unit 10.

Specifically, the swing analysis portion 215 computes an offset amount included in the measured data by using the measured data (acceleration data and angular velocity data) for the user 2 during standing still (at address), stored in the storage section 24. The swing analysis portion 215 generates the first attitude information of the hands 2a of the user 2 holding the golf club 3 during standing still with the first generator 211. Next, the swing analysis portion 215 subtracts the offset amount from measured data after starting the swing, stored in the storage section 24, so as to perform bias correction, and computes a position and an attitude of the sensor unit 10 during a swing action of the user 2 (during an action in step S106 in FIG. 5) by using the bias-corrected measured data. The swing analysis portion 215 (second generator 212) generates the second attitude information of the hands 2a of the user 2 holding the golf club 3 at impact. The swing analysis portion 215 (third generator 213) generates the attitude difference information between the first attitude information during standing still and the second attitude information at impact. As mentioned above, the third generator 213 generates the attitude difference information as information indicating a difference (a difference or a variation between attitudes) between an attitude of the hands 2a of the user 2 holding the golf club 3 during standing still and an attitude of the hands 2a of the user 2 holding the golf club 3 at impact.

For example, the swing analysis portion 215 (first generator 211) computes a position (initial position) of the sensor unit 10 during standing still (at address) of the user 2 in an XYZ coordinate system (global coordinate system) by using acceleration data measured by the acceleration sensor 12, the golf club information 242, and the sensor attachment position information 246, and integrates subsequent acceleration data so as to compute changes in positions from the initial position of the sensor unit 10 in a time series. Since the user 2 performs the action in step S103 in FIG. 5, an X coordinate of the initial position of the sensor unit 10 is 0. As illustrated in FIG. 2, since the y axis of the sensor unit 10 matches the longitudinal direction of the shaft of the golf club 3, and the acceleration sensor 12 measures only the gravitational acceleration during standing still of the user 2, the swing analysis portion 215 can compute an inclined angle of the shaft by using y axis acceleration data. The swing analysis portion 215 obtains a distance $L_{SH}$ (not illustrated) between the sensor unit 10 and the head 3a on the basis of the golf club information 242 (a length of the shaft), and the sensor attachment position information 246 (a distance from the grip), and sets, as the initial position of the sensor unit 10, a position of the sensor unit 10 at the distance $L_{SH}$ from the origin in a negative direction of the y axis of the sensor unit 10, specified by the inclined angle of the shaft when a position of the head is used as the origin (0,0,0). In other words, the first generator 211 obtains the first attitude information indicating a position of the hands 2a (refer to FIG. 1) of the user 2 during standing still.

The swing analysis portion 215 computes an attitude (initial attitude) of the sensor unit 10 during standing still (at address) of the user 2 in the XYZ coordinate system (global coordinate system) by using acceleration data measured by the acceleration sensor 12, and computes changes in attitudes from the initial attitude of the sensor unit 10 by performing rotation calculation using angular velocity data which is subsequently measured by the angular velocity sensor 14. An attitude of the sensor unit 10 may be expressed by, for example, rotation angles (a roll angle, a pitch angle, and a yaw angle) about the x axis, the y axis, and the z axis, or a quaternion. Since the acceleration sensor 12 measures only the gravitational acceleration during standing still of the user 2, the swing analysis portion 215 can specify angles respectively formed between the x axis, the y axis, and the z axis of the sensor unit 10, and the gravitational direction, by using three-axis acceleration data. Since the user 2 performs the action in step S103 in FIG. 5, the y axis of the sensor unit 10 is present on a YZ plane during standing still of the user 2, and thus the swing analysis portion 215 can specify the initial attitude of the sensor unit 10.

The swing analysis portion 215 may detect specific timings (for example, timings of swing starting, halfway back, a top, halfway down, and impact) during a swing action of the user 2. For example, the swing analysis portion 215 computes a combined value of measured data (acceleration data or angular velocity data) output from the sensor unit 10, and specifies timings (time points) of swing starting and a top on the basis of the combined value.

On the basis of a position of the sensor unit 10 at each time point (timing), an attitude of the sensor unit 10 at the time point, the golf club information 242, and the sensor attachment position information 246, the swing analysis portion 215 (second generator 212) computes a position of the head at the time point. The second generator 212 generates the second attitude information indicating a position of the hands 2a (refer to FIG. 1) of the user 2 at impact on the basis of the position of the sensor unit 10, and an attitude of the sensor unit 10 at a time point corresponding to impact. On the basis of a position of the sensor unit 10 at each time point of a swing, an attitude of the sensor unit 10 at the time point, the golf club information 242, and the sensor attachment position information 246, the swing analysis portion 215 computes a position of the grip at the time point. The swing analysis portion 215 generates swing trajectory data on the basis of obtained data regarding a series of swing actions.

The signal processing section 16 of the sensor unit 10 may compute an offset amount of measured data so as to perform bias correction on the measured data, and the acceleration sensor 12 and the angular velocity sensor 14 may have a bias correction function. In this case, it is not necessary for the swing analysis portion 215 to perform bias correction on the measured data.

The image data generation portion 216 performs a process of generating image data for displaying determination result information on the display section 25. The image data generation portion 216 performs a process of generating image data for displaying imaging data captured by the imaging section 27 or the recorder 50 on the display section 25 as an image.

The storage processing portion 217 performs a process of receiving time information and measured data from the data acquisition portion 210 and storing the time information and the measured data in the storage section 24 in correlation with each other. The storage processing portion 217 performs a process of storing imaging data captured by the imaging section 27 or the recorder 50 in the storage section 24.

The storage processing portion 217 performs read/write processes of various programs or various data for the storage section 24. The storage processing portion 217 performs not only the process of storing the time information and the measured data received from the data acquisition portion 210 in the storage section 24 in correlation with each other, but also a process of storing determination result information or the like generated by the swing analysis portion 215, in the storage section 24.

The display processing portion 218 performs a process of displaying various images (including text, symbols, and the like in addition to an image corresponding to the image data generated by the image data generation portion 216) on the display section 25. For example, the display processing portion 218 displays an image corresponding to the image data generated by the image data generation portion 216, or text or the like indicating a determination result in the swing analysis portion 215 automatically or in response to an input operation performed by the user 2 after a swing action of the user 2 is completed on the display section 25. Alternatively, a display section (not illustrated) may be provided in the sensor unit 10, or another display apparatus (not illustrated) may be provided, and the display processing portion 218 may transmit image data to the sensor unit 10 or other display apparatuses via the communication section 22, so that various images, text, or the like is displayed on the display section of the sensor unit 10 or another display apparatus.

The display section 25 may display, for example, at least one of the first attitude information and the second attitude information, or the attitude difference information indicating a difference (variation) between an attitude of the hands 2a of the user 2 holding the golf club 3 during standing still and an attitude of the hands 2a of the user 2 holding the golf club 3 at impact. The display section 25 may display virtual lines such as a first straight line 40 (refer to FIG. 8) based on the first attitude information or a second straight line 41 (refer to FIG. 8) based on the second attitude information. In this case, the display section 25 may display either the first straight line 40 or the second straight line 41, and may display both of the straight lines. The display section 25 may display a series of swing actions of the user 2 as a swing trajectory 30 (refer to FIGS. 6 and 8) or as swing images (moving images) based on imaging data captured by the imaging section 27 or the recorder 50.

Through the above-described display, it is possible to easily recognize a state of an attitude (position) related to the hands 2a of the user 2 during a swing, such as "hands-up" or "hands-down", or a difference between an attitude during standing still and an attitude at impact, by viewing the display section 25. Since the swing trajectory 30 (refer to FIGS. 6 and 8) of the user 2 is displayed, it is possible to easily visually recognize a series of swing actions. Consequently, it is possible to easily and objectively determine the quality or tendency of an attitude of the hands 2a of the user 2 holding the golf club 3 during a swing.

Figure 6:
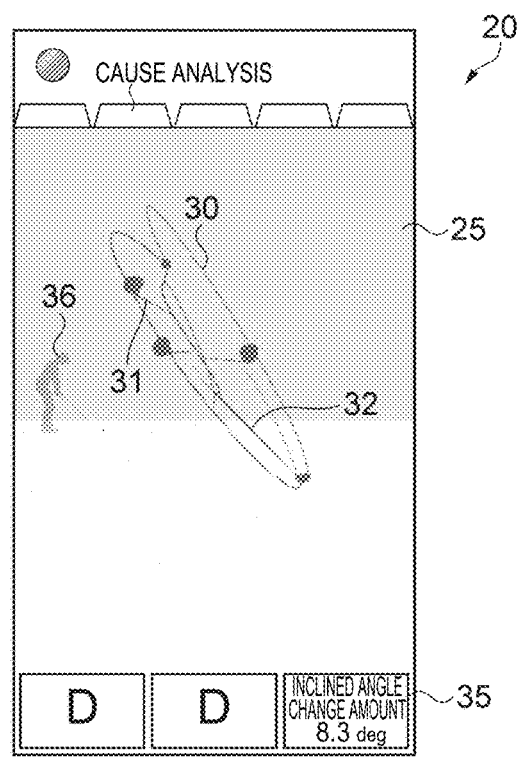
FIG. 6 is a diagram illustrating a display example 1 on a motion analysis display apparatus.

Here, the display on the display section 25 is preferably displayed as an image in a front view viewed from directions intersecting the hitting surface of the head 3a (refer to FIG. 1) of the golf club 3 (refer to FIG. 1) as an exercise equipment (refer to FIG. 6). The front view here may be either a front view viewed from the golf ball 4 side in a target direction of connecting a target to the golf ball 4 or a front view viewed from an opposite side (target side) to the golf ball 4 side in the target direction.

Through the above-described display, a state of an inclination (an inclination of the golf club 3) connecting the hands 2a of the user 2 to a position of the head 3a of the golf club 3 during standing still or at impact can be displayed on the display section 25 so as to be easily viewed and easily understood. Consequently, it is possible to easily perceive or point out a state (quality) of the inclination (an inclination of the golf club 3) or a variation in the inclination.

The sound output processing portion 219 performs a process of outputting various sounds (including voices, buzzer sounds, and the like) from the sound output section 26. For example, the sound output processing portion 219 may read the various pieces of information stored in the storage section 24 automatically or when a predetermined input operation is input after a swing action of the user 2 is completed, and may output a swing analysis sound or voice from the sound output section 26. Alternatively, the sound output section 26 may be provided in the sensor unit 10, and the sound output processing portion 219 may transmit various items of sound data or voice data to the sensor unit 10 via the communication section 22, and may output various sounds or voices from the sound output section of the sensor unit 10.

A vibration mechanism may be provided in the motion analysis display apparatus 20 or the sensor unit 10, and various pieces of information may be converted into vibration information by the vibration mechanism so as to be presented to the user 2.

The recorder 50 includes a communication section 52 which transmits image data captured by a video camera 51 to the motion analysis display apparatus (display apparatus) 20 or receives a control command from the motion analysis display apparatus 20. The video camera 51 captures images of swing actions of the user 2, and transmits captured image data to the communication section 52. The communication section 52 performs of transmitting the image data captured by the video camera 51 to the communication section 22 of the motion analysis display apparatus 20, or receiving a control command from the motion analysis display apparatus 20 and sending the control command to the video camera 51. The recorder 50 may not necessarily be provided in the swing analysis system 1. The recorder 50 is not limited to capturing moving image data, and may capture still image data.

According to the swing analysis system 1, attitude information of the hands 2a of the user (subject) 2 is displayed on the display section 25 of the motion analysis display apparatus 20 as a display apparatus on the basis of outputs from the inertial sensors (the acceleration sensor 12 and the angular velocity sensor 14) of the sensor unit 10. Specifically, either one of the first attitude information of the hands 2a of the user 2 during standing still, generated by the first generator 211, and the second attitude information of the hands 2a of the user 2 at impact, generated by the second generator 212, is displayed on the display section 25 of the motion analysis display apparatus 20. The attitude difference information between the first attitude information of the hands 2a of the user 2 holding the golf club 3 during standing still and the second attitude information of the hands 2a of the user 2 holding the golf club 3 at impact, generated by the third generator 213, is displayed on the display section 25 of the motion analysis display apparatus 20. Consequently, it is possible to easily recognize a state of an attitude related to the hands 2a of the user 2 during a swing, such as "hands-up" or "hands-down", or a difference between an attitude of the hands 2a of the user 2 holding the golf club 3 during standing still and an attitude of the hands 2a of the user 2 holding the golf club 3 at impact, by viewing the display section 25 of the motion analysis display apparatus 20. As mentioned above, by using the motion analysis display apparatus 20 (display apparatus), it is possible to easily and objectively determine the quality or tendency of an attitude of the hands 2a of the user 2 holding the golf club 3 during a swing.

1-3. Operation Procedures of Swing Analysis (Motion Analysis) System

Figure 5:
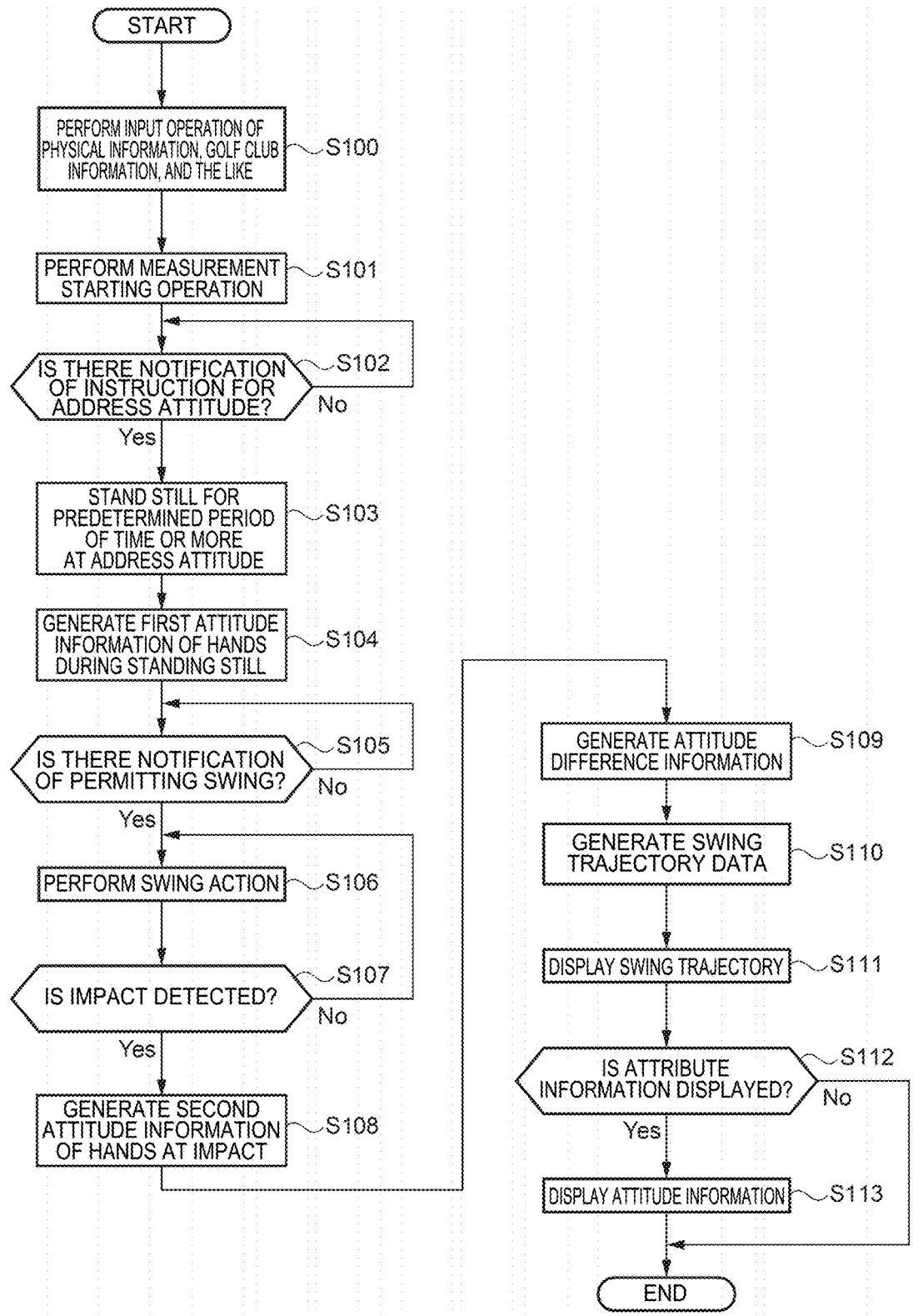
FIG. 5 is a flowchart illustrating operation procedures of the motion analysis system (swing analysis system).

Next, with reference to FIG. 5, a description will be made of operation procedures (analysis result display method) of the swing analysis (motion analysis) system 1, and swing actions of the user 2. A display method for the swing analysis (motion analysis) system 1 will also be described. The user (subject) 2 performs a series of swing actions for hitting the golf ball 4 as the target according to predefined procedures. FIG. 5 is a flowchart illustrating swing actions of the user 2, and swing analysis procedures performed by the swing analysis (motion analysis) system 1. In the following description of the procedures, the reference numerals used for the constituent elements of the swing analysis (motion analysis) system 1 are used. The following operation procedures may be realized by the swing analysis system 1 causing a computer to execute the swing analysis program (motion analysis program) 240.

As illustrated in FIG. 5, first, the user 2 performs an input operation of the physical information 244 of the user 2, information (golf club information) regarding the golf club 3 used by the user 2, and the like via the motion analysis display apparatus 20 (step S100). The physical information 244 may include at least one of information regarding a height, a length of the arms, and a length of the legs of the user 2, and may further include information regarding sex or other information. The golf club information 242 includes at least one of information regarding a length (club length) of the golf club 3 and the type (number) of golf club 3.

In step S100, the user 2 inputs physical information such as a height, the sex, age, and country as the physical information 244, and inputs golf club information such as a club length, and a club number as the golf club information 242. Information included in the physical information 244 is not limited thereto, and, the physical information may include, for example, at least one of information regarding a length of the arms and a length of the legs instead of or along with the height. Similarly, information included in the golf club information 242 is not limited thereto, and, for example, the golf club information may not include at least one of information regarding the club length and the club number, and may include other information.

Next, the user 2 performs a measurement starting operation (an operation for starting measurement in the sensor unit 10) via the motion analysis display apparatus 20 (step S101). If the user 2 performs the measurement starting operation in step S101, the sensor unit 10 (the inertial sensors) measures three-axis accelerations and three-axis angular velocities in a predetermined cycle (for example, 1 ms), and sequentially transmits the measured data to the motion analysis display apparatus 20. Communication between the sensor unit 10 and the swing analysis apparatus 20 may be wireless communication, and may be wired communication. This data indicates a position or an attitude of the sensor unit 10, and further indicates a position or an attitude of each portion of the golf club 3.

Next, after receiving a notification (for example, a notification using a voice) of giving an instruction for taking an address attitude (a basic attitude before starting a motion) from the motion analysis display apparatus 20 (Yes in step S102), the user 2 takes an address attitude so that the axis in the longitudinal direction of the shaft of the golf club 3 is perpendicular to a target direction (target hit ball direction), and stands still for a predetermined period of time or more (step S103). Here, the first generator 211 of the motion analysis display apparatus 20 generates (acquires) the first attitude information of the hands 2a of the user 2 during standing still by using measured data output from the sensor unit 10 (step S104). In a case where the notification (for example, a notification using a voice) of giving an instruction for taking an address attitude (a basic attitude before starting a motion) from the motion analysis display apparatus 20 is not received (No in step S102), the user 2 waits for the notification to be received.

Next, the user 2 receives a notification (for example, a notification using a voice) of permitting a swing from the motion analysis display apparatus 20 (Yes in step S105), and then hits the golf ball 4 as the target by performing a swing action (step S106). In a case where there is no notification (for example, a notification using a voice) of permitting a swing from the motion analysis display apparatus 20 (No in step S105), the user 2 delays a swing action until the notification of permitting a swing is received.

Next, in a case where the user 2 performs the swing action in step S106, and then an impact timing is detected on the basis of swing analysis in the motion analysis display apparatus 20 (Yes in step S107), the second generator 212 of the motion analysis display apparatus 20 generates (acquires) the second attitude information of the hands 2a of the user 2 at impact by using measured data output from the sensor unit 10 (step S108). In a case where an impact timing is not detected by the motion analysis display apparatus 20 (No in step S107), checking of whether or not an impact timing is detected is repeatedly performed.

Next, the third generator 213 of the motion analysis display apparatus 20 generates (acquires) the attitude difference information indicating a difference between attitudes (a difference or a variation between attitudes) of the hands 2a of the user 2 holding the golf club 3 as attitude difference information between the first attitude information during standing still and the second attitude information at impact (step S109).

Next, the swing analysis portion 215 of the motion analysis display apparatus 20 generates (acquires) swing trajectory information on the basis of obtained data of a series of swing actions after the user 2 performs a series of swing actions (step S110).

Next, the motion analysis display apparatus 20 displays the swing trajectory information (image) generated in step S110, on the display section 25 (step S111).

Next, in step S112, the motion analysis display apparatus 20 checks whether or not there is an instruction for displaying the attitude information or the attitude difference information on the display section 25, and proceeds to the next step S113 in a case where there is the display instruction (Yes in step S112). Here, in a case where there is no display instruction (No in step S112), a series of operation procedures is finished.

Next, in a case where there is the instruction for displaying the attitude information in step S112 (Yes in step S112), the motion analysis display apparatus 20 displays the attitude information on the display section 25 (step S113). Here, the displayed attitude information includes the first attitude information of the hands 2a of the user 2 during standing still, generated in step S104, the second attitude information of the hands 2a of the user 2 at impact, generated in step S108, and the attitude difference information generated in step S109. In step S113, at least one of the first attitude information generated in step S104 and the second attitude information generated in step S108 is displayed. The attitude difference information displayed in step S113 may be displayed to overlap the swing trajectory information (image) displayed in step S111, and may be displayed through switching between screens of the attitude difference information and the swing trajectory information (image).

Through the above-described steps, a series of operation procedures of the swing analysis (motion analysis) system 1 and the user 2 are finished.

A step of imaging swing actions of the user 2 may be included in the operation procedures of the swing analysis (motion analysis) system 1. For example, captured images such as video images (moving image data) may be displayed on the display section 25 in step S113. As mentioned above, captured swing images of the user 2 are displayed on the display section 25, and thus a series of swing actions can be viewed as images. Consequently, it is possible to determine swing actions of the user 2 while viewing the swing actions as images.

Figure 7:
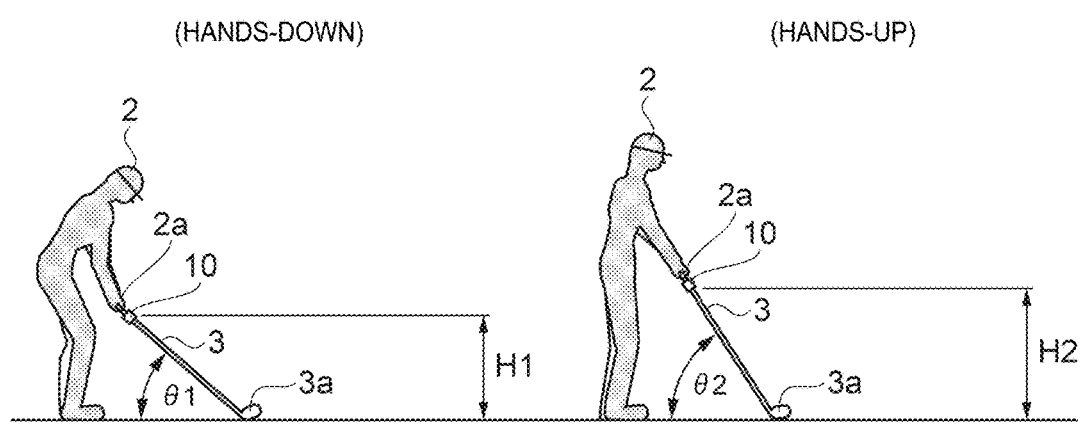
FIG. 7 is a diagram for explaining an attitude of the hands at address.
Figure 8:
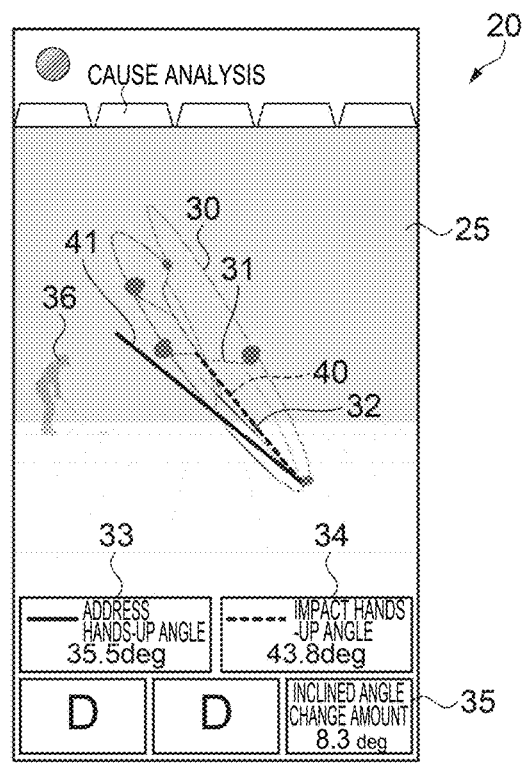
FIG. 8 is a diagram illustrating a display example 2 on the motion analysis display apparatus.

Here, display examples of information displayed on the display section 25 in step S111 or step S113 will be described with reference to FIGS. 6, 7 and 8. FIG. 6 is a diagram illustrating a display example 1 of attitude information on the display section 25 of the motion analysis display apparatus 20, FIG. 7 is a diagram for explaining an attitude of the hands 2a at address, and FIG. 8 is a diagram illustrating a display example 2 of attitude information on the display section 25 of the motion analysis display apparatus 20.

First, with reference to FIG. 6, a description will be made of the display example 1 of information displayed on the display section 25 of the motion analysis display apparatus

20. In the display example 1 illustrated in FIG. 6, information is displayed on the display section 25 of the motion analysis display apparatus 20. A series of swing actions of the user 2 is displayed as the swing trajectory 30 on the display section 25. In display of the swing trajectory 30, a trajectory of a series of swing actions is displayed by displaying a state of the golf club at each time point (timing), for example, a golf club image 31 during a backswing, with a golf club image 32 at address as a swing starting timing. The golf club image 32 may be an image at impact.

In this example, the swing trajectory 30 is displayed as an image viewed from the rear side, that is, an image viewed from an opposite side to the golf ball 4 side among front views viewed from directions intersecting the hitting surface of the golf ball 4 (refer to FIG. 1) of the head 3a (refer to FIG. 1) of the golf club 3 (refer to FIG. 1). As a mark indicating this viewing direction, a mark 36 is displayed. Regarding a display direction, an image viewed from the golf ball 4 side may be displayed.

A display window 35 showing attitude difference information indicating a difference between an attitude (position) of the hands 2a of the user 2 holding the golf club 3 during standing still and an attitude (position) of the hands 2a of the user 2 holding the golf club 3 at impact may be displayed on a part of the display section 25 (a lower right part in the screen in this example). The display device 35 showing the attitude difference information here displays a difference between inclined angles formed between the shaft of the golf club 3 and the ground illustrated in FIG. 7 during standing still and at impact, as an "inclined angle change amount". Since such numerical value information is also displayed, it is possible to easily and accurately understand a difference (attitude difference) between attitudes (positions) of the hands 2a of the user 2 during standing still and at impact.

Next, with reference to FIG. 8, a description will be made of the display example 2 of information displayed on the display section 25 of the motion analysis display apparatus 20. In the display example 2 illustrated in FIG. 8, information is displayed on the display section 25 of the motion analysis display apparatus 20 in the same manner as the display example 1. In a series of swing actions of the user 2, the swing trajectory 30 which approximates the swing actions, the first straight line 40 which is a virtual line indicating a state of the golf club 3 based on the first attitude information, that is, a state of the golf club 3 during standing still, and the second straight line 41 which is a virtual line indicating a state of the golf club 3 based on the second attitude information, that is, a state of the golf club 3 at impact are displayed on the display section 25. The swing trajectory 30 and a mark 36 indicating a viewing direction are displayed in the same manner as in the above-described display example 1, and thus will not be described here. At least one of the first straight line 40 and the second straight line 41 may be displayed. As mentioned above, an attitude (position) of the hands 2a (refer to FIG. 7) of the user 2 or an attitude of the golf club 3 as an exercise equipment can be represented according to either one of the first straight line 40 and the second straight line 41 displayed on the display section 25, and thus it is possible to easily visually recognize an attitude (position) of the hands 2a of the user 2 or an attitude of the golf club 3.

Display windows 33 and 34 showing attitudes (positions) of the hands 2a of the user 2 holding the golf club 3 during standing still and impact as inclined angles (a hands-down angle and a hands-up angle) of the golf club 3 (refer to FIG. 7), and a display window 35 showing attitude difference information indicating a difference between attitudes (a difference between positions) of the hands 2a during standing still and at impact are displayed on a part of the display section 25 (a lower right part in the screen in this example). The display window 33 in this example displays a hands-up angle "35.5 deg" as an inclined angle of the golf club 3 in a case where an attitude (position) of the hands 2a of the user 2 during standing still is in a hands-up state. The display window 34 displays a hands-up angle "43.8 deg" as an inclined angle of the golf club 3 in a case where an attitude (position) of the hands 2a of the user 2 at impact is in a hands-up state. The display window 35 showing the attitude difference information displays an attitude difference (position difference) between the hands-up angle "35.5 deg" during standing still and the hands-up angle "43.8 deg" at impact, as an "inclined angle change amount". Since such numerical value information is also displayed, it is possible to easily and accurately understand attitudes (positions) of the hands 2a of the user 2 during standing still and impact, and a difference (attitude difference) between attitudes (positions) of the hands 2a of the user 2 during standing still and at impact.

Hereinafter, with reference to FIG. 7, a hands-down angle and a hands-up angle will be described. As illustrated in FIG. 7, an attitude (position) of the hands 2a of the user 2 holding the golf club 3 includes a hands-down state in which a position of the hands 2a is low, and a hands-up state in which a position of the hands 2a is high. In the hands-down state, an inclined angle of the golf club 3 is obtained on the basis of a position (height H1) of the sensor unit 10 interlocking with a position of the hands 2a, and a length from a position where the sensor unit 10 is attached to the head 3a, and this angle θ1 is used as a hands-down angle. In the hands-up state, in the same manner as described above, an inclined angle of the golf club 3 is obtained on the basis of a position (height H1) of the sensor unit 10 interlocking with a position of the hands 2a, and a length from a position where the sensor unit 10 is attached to the head 3a, and this angle θ2 is used as a hands-up angle.

Display is performed as in the display example 2, and thus it is possible to easily recognize a state of an attitude related to the hands 2a of the user 2 during a swing, such as "hands-up" or "hands-down", or a difference between an attitude during standing still and an attitude at impact, by viewing the display section 25. Since the swing trajectory 30 of the user 2 is displayed, it is possible to easily visually recognize a series of swing actions. Consequently, it is possible to easily and objectively determine the quality of an attitude of the hands 2a of the user 2 holding the golf club 3 during a swing.

Other advice information based on swing analysis results, for example, a text image representing a swing type of the user 2 or a text image representing advice (practice method or the like) suitable for the swing type of the user 2 may be displayed on the display section 25. Moving images as video pictures may be displayed on the display section 25.

The first straight line 40, the second straight line 41, the display windows 33 and 34, and the display window 35 showing the attitude difference information may be displayed to overlap the swing trajectory 30 or the golf club image 32, and may be displayed through switching between display screens, as in the display example 2.

Figure 9:
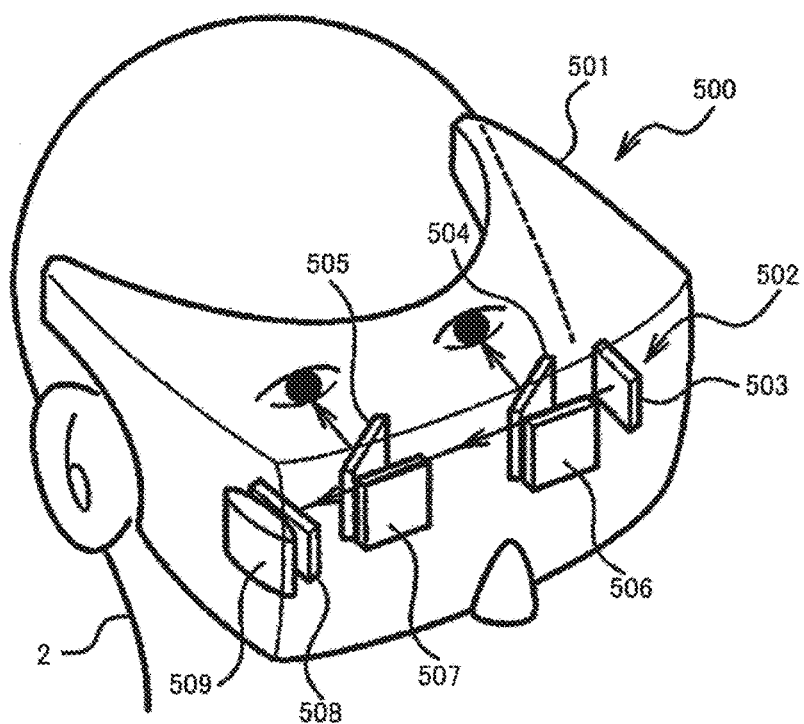
FIG. 9 is a perspective view illustrating a head mounted display as an example of the motion analysis display apparatus.

Next, with reference to FIG. 9, a description will be made of an example of using a head mounted display (HMD) as the motion analysis display apparatus 20. FIG. 9 is a perspective view illustrating a head mounted display (HMD) as a motion analysis display apparatus.

1-4. Application 1 of Motion Analysis Display Apparatus

As illustrated in FIG. 9, a head mounted display (HMD) 500 includes a spectacle main body 501 mounted on the head of the user 2. The spectacle main body 501 is provided with a display section 502. The display section 502 integrates a light beam emitted from an image display unit 503 with a light beam directed toward the eyes of the user 2, and thus overlaps a virtual image on the image display unit 503 with a real image of the external world viewed from the user 2.

The display section 502 is provided with, for example, the image display unit 503 such as an liquid crystal display (LCD), a first beam splitter 504, a second beam splitter 505, a first concave reflection mirror 506, a second concave reflection mirror 507, a shutter 508, and a convex lens 509.

The first beam splitter 504 is disposed on the front side of the left eye of the user 2, and partially transmits and partially reflects light emitted from the image display unit 503. The second beam splitter 505 is disposed on the front side of the right eye of the user 2, and partially transmits and partially reflects light which is partially transmitted from the first beam splitter 504.

The first concave reflection mirror 506, which is disposed in front of the first beam splitter 504, partially reflects the partially reflected light from the first beam splitter 504 so as to transmit the light through the first beam splitter 504, and thus guides the light to the left eye of the user 2. The second concave reflection mirror 507, which is disposed in front of the second beam splitter 505, partially reflects the partially reflected light from the second beam splitter 505 so as to transmit the light through the second beam splitter 505, and thus guides the light to the right eye of the user 2.

The convex lens 509 guides partially transmitted light from the second beam splitter 505 to the outside of the head mounted display (HMD) 500 when the shutter 508 is opened.

The swing information such as the swing trajectory 30 (refer to FIGS. 6 and 8) approximating the swing actions, and swing attitude information such as attitudes (positions) of the hands 2a, in a series of swing actions of the user 2, as described in the display example 1 or the display example 2, are displayed on the head mounted display (HMD) 500. The display content is the same as in the display example 1 or the display example 2, and a detailed description thereof will be omitted.

According to the head mounted display (HMD) 500, since the head mounted display (HMD) is mounted on the head and displays information, the user 2 can understand swing information of the user or attitude (position) information of the hands 2a without holding the motion analysis display apparatus 20 including the display section 25 displaying information with the hands.

The head mounted display (HMD) 500 may have the functions of the motion analysis display apparatus 20 and may display swing analysis or swing information based on measured data from the sensor unit 10, and may be used as a display section displaying image data transmitted from the separate motion analysis display apparatus 20. The functions of the motion analysis display apparatus (display apparatus) 20 include the processing section 21 (an example of a processing section), the communication section 22, the operation section 23, the storage section 24, the display section 25, the sound output section 26, and the imaging section 27 as described above.

Figure 10:
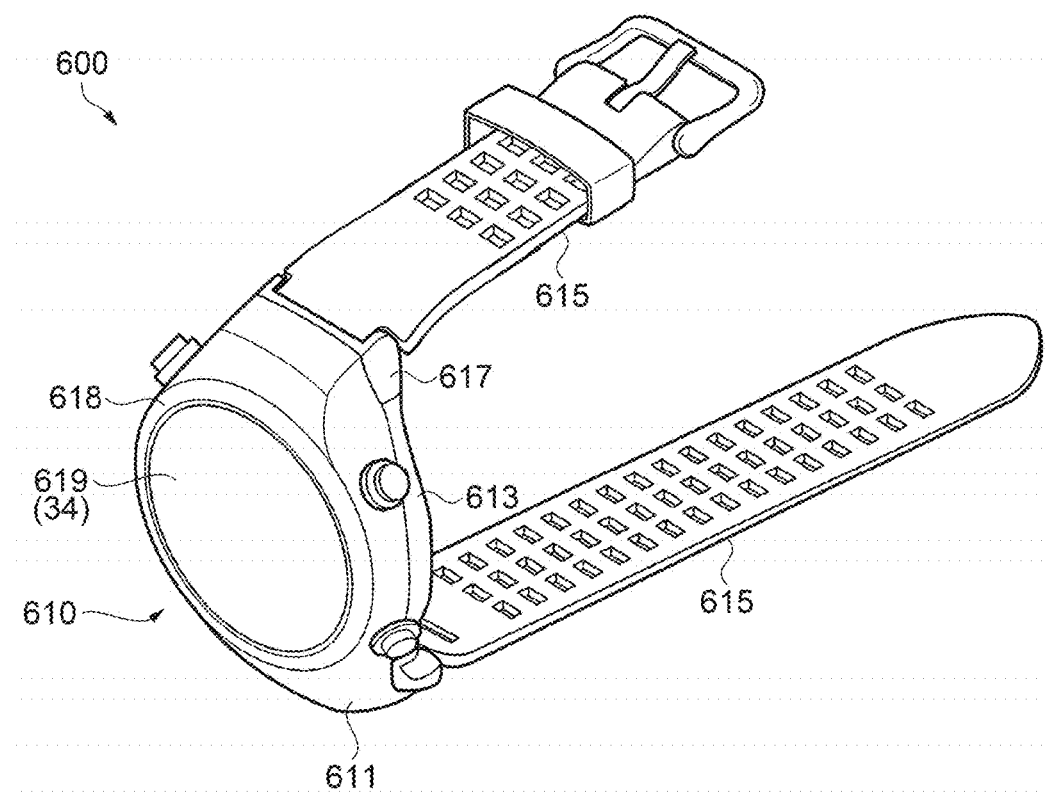
FIG. 10 is a perspective view illustrating an arm mounted motion analysis display apparatus as an example of a wearable apparatus.

Next, with reference to FIG. 10, a description will be made of an example of using an arm mounted analysis display apparatus as an example of a wearable apparatus, as the motion analysis display apparatus. FIG. 10 is a perspective view illustrating an arm mounted motion analysis display apparatus as an example of a wearable apparatus.

1-5. Application 2 of Motion Analysis Display Apparatus

As illustrated in FIG. 10, a wearable (arm mounted) analysis display apparatus 600 is mounted on a predetermined part (the wrist in this example) of the user (subject) 2 (refer to FIG. 1) and displays swing analysis or swing information based on measured data from the sensor unit 10 (refer to FIG. 1). The analysis display apparatus 600 includes an apparatus main body 610 which is worn by the user 2 and displays swing analysis information such as swing analysis or attitude information of the hands 2a (refer to FIG. 1) of the user 2, and a band portion 615 which is attached to the apparatus main body 610 and allows the apparatus main body 610 to be mounted on the user 2.

The apparatus main body 610 of the analysis display apparatus 600 is provided with a bottom case 613 on the side mounted on the user 2, and a top case 611 on an opposite side to the side mounted on the user 2. A bezel 618 is provided on a top side (top case 611) of the apparatus main body 610, and a glass plate 619 as a top plate portion (outer wall) which is disposed inside the bezel 618 and protects inner structures is also provided. A pair of band attachment portions 617 which is a connection portion with the band portion 615 are provided on both sides of the bottom case 613.

The apparatus main body 610 is provided with a display portion such as a liquid crystal display (LCD 634) directly under the glass plate 619. The user 2 can view swing analysis information, attitude information of the hands 2a of the user 2, or the like, displayed on the liquid crystal display (LCD 634) via the glass plate 619. The apparatus main body 610 may include the processing section 21, the communication section 22, the operation section 23, the storage section 24, the display section 25, the sound output section 26, and the imaging section 27, in the same manner as the motion analysis display apparatus 20 described with reference to FIG. 4. The display section 25 corresponds to a display portion such as the liquid crystal display (LCD 634) in this example.

The swing information such as the swing trajectory 30 (refer to FIGS. 6 and 8) approximating the swing actions, and swing attitude information such as attitudes (positions) of the hands 2a, in a series of swing actions of the user 2, as described in the display example 1 or the display example 2, are displayed on the display portion of the liquid crystal display (LCD 634). The display content is the same as in the display example 1 or the display example 2, and a detailed description thereof will be omitted.

Other advice information based on swing analysis results, for example, a text image representing a swing type of the user 2 or a text image representing advice (practice method or the like) suitable for the swing type of the user 2 may be displayed on the display portion of the liquid crystal display (LCD 634). Moving images as video pictures may be displayed on the display portion of the liquid crystal display (LCD 634).

In the above description, an example in which the top plate portion of the apparatus main body 610 is implemented by the glass plate 619 has been described, but the top plate portion may be formed by using materials other than glass, such as transparent plastic, as long as a member is transparent so as to allow the LCD 634 to be viewed, and has the rigidity of being capable of protecting constituent elements included in the top case 611 and the bottom case 613, such as the LCD 634. A configuration example in which the bezel 618 is provided has been described, but the bezel 618 may not be provided.

According to the wearable (arm mounted) analysis display apparatus 600, since analysis display apparatus is mounted on the arm and displays information, the user 2 can understand swing information of the user or attitude (position) information of the hands 2a without holding the display portion (liquid crystal display (LCD 634)) displaying information with the hands.

The wearable (arm mounted) analysis display apparatus 600 may have the functions of the motion analysis display apparatus 20 and may display swing analysis or swing information based on measured data from the sensor unit 10, and may be used as a display section displaying image data transmitted from the separate motion analysis display apparatus 20. The functions of the motion analysis display apparatus (display apparatus) 20 include the processing section 21 (an example of a processing section), the communication section 22, the operation section 23, the storage section 24, the display section 25, the sound output section 26, and the imaging section 27 as described in the motion analysis display apparatus (display apparatus) 20 of the present embodiment.

For example, one or more embodiments of the invention include substantially the same configuration (for example, a configuration in which functions, methods, and results are the same, or a configuration in which objects and effects are the same) as the configuration described in the embodiment. The various embodiments of the invention include a configuration in which an inessential part of the configuration described in the embodiment is replaced with another part. The various embodiments of the invention include a configuration which achieves the same operation and effect or a configuration capable of achieving the same object as in the configuration described in the embodiment. The various embodiments of the invention include a configuration in which a well-known technique is added to the configuration described in the embodiment.

What is claimed is:

1. A display method comprising:
    acquiring first attitude information of a golf club at address attitude on the basis of an output from an inertial sensor which is attached on a shaft of the golf club and measures swing actions of a subject who performs a swing with the golf club;
    acquiring second attitude information of the golf club at impact on the basis of an output from the inertial sensor;
    determining a first inclined angle at the address attitude based upon the first attitude information and a length from a position where the inertial sensor is attached to a head of the golf club;
    determining a second inclined angle at the impact based upon the second attitude information and the length from the position where the inertial sensor is attached to the head of the golf club;
    determining an inclined angle change amount based upon the first inclined angle and the second inclined angle; and
    displaying the inclined angle change amount and at least one of the first attitude information and the second attitude information.

2. The display method according to claim 1,
    wherein, in the displaying, attitude difference information between the first attitude information and the second attitude information is displayed.

3. The display method according to claim 1, further comprising:
    acquiring a swing trajectory of the subject on the basis of an output from the inertial sensor,
    wherein, in the displaying, the swing trajectory is displayed.

4. The display method according to claim 1, further comprising:
    capturing an image of a swing of the subject,
    wherein, in the displaying, the captured image of the swing is displayed.

5. The display method according to claim 1,
    wherein, in the displaying, at least one of a first straight line based on the first attitude information and the second straight line based on the second attitude information is displayed.

6. The display method according to claim 1,
    wherein, in the displaying, information is displayed in a front view viewed from a direction intersecting a hitting surface of the golf club.

7. The display method according to claim 6,
    wherein the front view is a front view viewed from a target side or a front view viewed from an opposite side to the target side.

8. A display apparatus comprising:
    a processor configured to act as:
        a first generation section that generates first attitude information of a golf club at address attitude on the basis of an output from an inertial sensor which is attached on a shaft of the golf club and measures swing actions of the subject who performs a swing with the golf club;
        a second generation section that generates second attitude information of the golf club at impact on the basis of an output from the inertial sensor; and
        a determination section that determines (1) a first inclined angle at the address attitude based upon the first attitude information and a length from a position where the inertial sensor is attached to a head of the golf club, (2) a second inclined angle at the impact based upon the second attitude information and the length from the position where the inertial sensor is attached to the head of the golf club, and (3) an inclined angle change amount based upon the first inclined angle and the second inclined angle; and
    a display section that displays the inclined angle change amount and at least one of the first attitude information and the second attitude information.

9. The display apparatus according to claim 8, wherein the display section displays attitude difference information between the first attitude information and the second attitude information.

10. The display apparatus according to claim 8,
    wherein the display section displays a swing trajectory of the subject.

11. The display apparatus according to claim 8, further comprising:
    an imaging section that captures an image of the swing of the subject,
    wherein the display section displays the captured image of the swing.

12. The display apparatus according to claim 8,
    wherein the display section displays at least one of a first straight line based on the first attitude information and the second straight line based on the second attitude information.

13. The display apparatus according to claim 8,
wherein the display section displays information in a front view viewed from a direction intersecting a hitting surface of the golf club.

14. The display apparatus according to claim 13,
wherein the front view is a front view viewed from a target side or a front view viewed from an opposite side to the target side.

15. A motion analysis system comprising:
the display apparatus according to claim 8; and
the inertial sensor.

16. A motion analysis system comprising:
the display apparatus according to claim 9; and
the inertial sensor.

17. A motion analysis system comprising:
the display apparatus according to claim 10; and
the inertial sensor.

18. A motion analysis system comprising:
the display apparatus according to claim 11; and
the inertial sensor.

19. A motion analysis system comprising:
the display apparatus according to claim 12; and
the inertial sensor.

20. A non-transitory computer readable recording medium storing a program causing a computer to execute:
acquiring first attitude information of a golf dub at address attitude on the basis of an output from an inertial sensor which is attached on a shaft of the golf club and which measures swing actions of the subject who performs a swing with the golf club;
acquiring second attitude information of the golf club at impact on the basis of an output from the inertial sensor;
determining an inclined angle based upon a height of the inertial sensor in interlocking with a position of the hands of the subject, and a length from a position where the inertial sensor is attached to a head of the exercise equipment;
determining a first inclined angle at the address attitude based upon the first attitude information and a length from a position where the inertial sensor is attached to a head of the golf club;
determining a second inclined angle at the impact based upon the second attitude information and the length from the position where the inertial sensor is attached to the head of the golf club;
determining an inclined angle change amount based upon the first inclined angle and the second inclined angle; and
displaying the inclined angle chance amount and at least one of the first attitude information and the second attitude information.

21. A swing analysis system comprising:
a sensor unit configured to be coupled to a golf club, the sensor unit including an inertial sensor; and
a display apparatus that includes a processor and a display, wherein
the processor is configured to receive output data from the sensor unit and analyze a swing of the object by the subject based on the output data, including to compute an attitude of the sensor unit at different time points including first attitude information of the sensor unit during standing still of the subject indicating a position of the golf club at address attitude and second attitude information of the sensor indicating a position of the golf club at an impact by the golf dub;
the processor is configured to determine a first inclined angle at the address attitude based upon the first attitude information and a length from a position where the inertial sensor is attached to a head of the golf club;
the processor is configured to determine a second inclined angle at the impact based upon the second attitude information and the length from the position where the inertial sensor is attached to the head of the golf club;
the processor is configured to determine an inclined angle change amount based upon the first inclined angle and the second inclined angle; and
the display is configured to display the inclined angle change amount and at least one of the first attitude information and the second attitude information.

22. The swing analysis system according to claim 21,
wherein the processor is configured to act as a swing analysis portion configured to detect plural timings during a swing action of the user and on the basis of a position of the sensor unit at different time points of the plural timings, the attitude of the sensor unit at the different time points, object information indicating a type of object being swung and sensor attachment position information indicating an attachment position of the sensor unit to the object, compute changes in positions from an initial position of the sensor unit in a time series.

23. The swing analysis system according to claim 21,
wherein the sensor unit comprises a three-axis acceleration sensor and an angular velocity sensor.

24. The swing analysis system according to claim 21, further comprising:
an imaging section, wherein the display is configured to display a series of swing actions of the subject as one of a swing trajectory based on the computed attitude or swing images based on imaging data captured by the imaging section.

25. The swing analysis system according to claim 21,
wherein the display is configured to display a front view of the object and a state of inclination connecting the hands of the subject to a position of a portion of the object during standing still or impact.

26. The swing analysis system according to claim 21,
wherein the display is configured to display a attitude difference information between the first attitude information and the second attitude information on a portion of the display and wherein the inclined angle change amount includes numerical value information representing a change in inclined angles formed between a portion of the object and the ground during standing still and impact, the inclined angle change amount being displayed on another portion of the display.

27. The swing analysis system according to claim 21,
wherein the display is configured to be worn by the subject.

28. The swing analysis system according to claim 21,
wherein the display is configured to display a text image representing a swing type of the subject or advice suitable for the swing type of the subject.

* * * * *